US012709573B2

(12) United States Patent
Srubar, III et al.

(10) Patent No.: US 12,709,573 B2
(45) Date of Patent: Aug. 18, 2026

(54) METHODS OF FORMING MINERALS USING BIOMINERALIZING MICROORGANISMS AND BIOMINERALIZING MACROORGANISMS AND COMPOSITIONS FORMED USING SAME

(71) Applicant: The Regents of the University of Colorado, a body corporate, Denver, CO (US)

(72) Inventors: Wilfred V. Srubar, III, Boulder, CO (US); Sarah Lynn Williams, Boulder, CO (US); Jeffrey Cameron, Erie, CO (US); Mija Hubler, Boulder, CO (US); Sherri Cook, Boulder, CO (US); Aparna Nagarajan, Denver, CO (US); Chelsea Heveran, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 638 days.

(21) Appl. No.: 17/773,448

(22) PCT Filed: Oct. 30, 2020

(86) PCT No.: PCT/US2020/058344
§ 371 (c)(1),
(2) Date: Apr. 29, 2022

(87) PCT Pub. No.: WO2021/087350
PCT Pub. Date: May 6, 2021

(65) Prior Publication Data

US 2022/0371953 A1 Nov. 24, 2022

Related U.S. Application Data

(60) Provisional application No. 62/928,944, filed on Oct. 31, 2019.

(51) Int. Cl.
*C04B 14/06* (2006.01)
*C04B 14/08* (2006.01)
(Continued)

(52) U.S. Cl.
CPC .............. *C04B 14/08* (2013.01); *C04B 14/06* (2013.01); *C04B 14/28* (2013.01); *C04B 28/04* (2013.01);
(Continued)

(58) Field of Classification Search
CPC ......... C04B 14/08; C04B 14/06; C04B 14/28; C04B 28/14; C04B 2103/0001;
(Continued)

(56) References Cited

U.S. PATENT DOCUMENTS 11,566,264 B2 1/2023 Sarraf
2019/0112228 A1* 4/2019 Ozersky ................ C04B 18/022

FOREIGN PATENT DOCUMENTS

CN 101302484 B 11/2008
CN 101759410 A * 6/2010 ............. C04B 28/00
(Continued)

OTHER PUBLICATIONS

Zhu et al. Assessment of *cyanobacterial* species for carbonate precipitation on mortar surface under different conditions. Ecological Engineering. 120,154-163. (Year: 2018).*
(Continued)

*Primary Examiner* — Amber R Orlando
*Assistant Examiner* — Anastasia A. Kuvayskaya
(74) *Attorney, Agent, or Firm* — Snell & Wilmer L.L.P.

(57) ABSTRACT

Methods of forming cement pastes, methods of forming concrete, and methods of forming other compositions using mineral particles formed from the one or more of biomineralizing microorganisms and biomineralizing microorganisms. Desired features, such as size and morphology, can be
(Continued)

controlled by controlling growth parameters of the biomineralizing microorganisms and biomineralizing microorganisms.

18 Claims, 8 Drawing Sheets

(51) Int. Cl.

| | |
|---|---|
| ***C04B 14/28*** | (2006.01) |
| ***C04B 28/04*** | (2006.01) |
| ***C09C 1/02*** | (2006.01) |
| ***C09C 1/30*** | (2006.01) |
| ***C09C 3/00*** | (2006.01) |
| ***C09C 3/04*** | (2006.01) |
| ***C12N 1/12*** | (2026.01) |
| ***C12N 1/20*** | (2026.01) |
| *C04B 103/00* | (2006.01) |

(52) U.S. Cl.
CPC ............ *C09C 1/021* (2013.01); *C09C 1/3018* (2013.01); *C09C 1/3027* (2013.01); *C09C 3/006* (2013.01); *C09C 3/041* (2013.01); *C09C 3/043* (2013.01); *C12N 1/12* (2013.01); *C12N 1/20* (2013.01); *C04B 2103/0001* (2013.01)

(58) Field of Classification Search
CPC ......... C04B 7/00; C09C 1/021; C09C 1/3018; C09C 3/006; C09C 3/041; C09C 3/043; C12N 1/12; C12N 1/20; C12R 2001/89; C12P 3/00
See application file for complete search history.

(56) References Cited

FOREIGN PATENT DOCUMENTS

| | | | | | |
|---|---|---|---|---|---|
| CN | 107384971 | A | | 11/2017 | |
| CN | 109320144 | A | | 2/2019 | |
| KR | 20130055964 | A | | 5/2013 | |
| KR | 101291725 | B1 | * | 7/2013 | ............. C04B 14/28 |
| WO | 199529250 | A1 | | 11/1995 | |
| WO | WO-2010048457 | A1 | * | 4/2010 | .............. C01F 11/18 |
| WO | 2016081509 | A1 | | 5/2016 | |

OTHER PUBLICATIONS

Jacob et al. Biogenic calcite particles from microalgae—Coccoliths as a potential raw material. Engineering in Life Sciences. 17, 605-612 (Year: 2017).*
Gröger et al. Biomolecular self-assembly and its relevance in silica biomineralization. Cell Biochem Biophys. 50, 23-39 (Year: 2008).*
Afifudin et al. Microorganism precipitation in enhancing concrete properties. Applied Mechanics and Materials. 1157-1165. (Year: 2011).*
Telschow et al. Cement formation—a success story in a black box: high temperature phase formation of Portland cement clinker. Industrial and Engineering Chemistry Research. 51, 10983-11004. (Year: 2012).*
CN 101759410 A Machine Translation (Year: 2010).*
KR 101291725_Machine Translation (Year: 2013).*
Durak et al. The role of the cytoskeleton in biomineralization in haptophyte algae, Scientific Reports, 7, 15409 (Year: 2017).*
KR 201291725_Machine Translation (Year: 2013).*
Zhu et al. Assessment of *cyanobacterial* species for carbonate precipitation on mortar surface under different conditions, Ecological Engineering, 120, pp. 154-163 (Year: 2018).*
Jacob et al. Biogenic calcite particles from microalgae—Coccoliths as a potential raw material, Engineering in Life Sciences, 17, pp. 605-612 (Year: 2017).*
Durak et al. The role of cyctoskeleton in biomineralization in haptophyte algae, Scientific Reports, 2017, 7: 15409 (Year: 2017).*
F/2 medium product description retrieved from https://utex.org/products/f-2-medium?variant=31722216915034 on May 1, 2025 (Year: 2025).*
Benzerara et al. Intracellular Ca-carbonate biomineralization is widespread in cyanobacterial, PNAS, vol. 111, 30, pp. 10933-10938 (Year: 2014).*
Telschow et al. Cement formation—a success story in a black box: high temperature phase formation of Portland cement clinker, Industrial and Engineering Chemistry Research, 51, pp. 10983-11004 (Year: 2012).*
Ariyanti et al., Feasibility of Using Microalgae for Biocement Production through Biocementation, Journal of Bioprocessing & Biotechniques, 2012, vol. 2, Issue 1, 4 pp.
Zhu et al., Potential application of biomineralization by Synechococcus PCC8806 for concrete restoration, Ecological Engineering 82 (2015), pp. 459-468.
Irfan et al., Optimization of bio-cement production from cement kiln dust using microalgae, Biotechnology Reports 23 (2019) e00356, 13 pp. [including an update to the article at the end].
EPO; Extended European Search Report mailed Nov. 24, 2023 in corresponding European Appl. No. 20883013.3.
CNIPA; Notice of Second Office Action mailed Dec. 5, 2023 in Chinese Application No. 202080090976.6.
EPO; Communication pursuant to Rules 70(2) and 70a(2) EPC mailed Dec. 12, 2023 in corresponding European Appl. No. 20883013.3.
Dhami et al., "Biomineralization of calcium carbonates and their engineered applications: a review" Frontiers in microbiology. Oct. 29, 2013;4:314 (13 pages).
Ghosh et al., "Sporosarcina pasteurii can form nanoscale calcium carbonate crystals on cell surface" PloS one 14.1 (Jan. 2019): e0210339 (15 pages).
Heveran et al., "Engineered ureolytic microorganisms can tailor the morphology and nanomechanical properties of microbial-precipitated calcium carbonate" Scientific reports 9.1 (Oct. 2019): 14721 (13 pages).
International Search Report with Written Opinion issued in International Application No. PCT/US2020/058344; Application Filing Date Oct. 30, 2020; Date of Mailing Mar. 3, 2021 (11 pages).
Liang et al., "Rational control of calcium carbonate precipitation by engineered *Escherichia coli*" ACS Synthetic Biology 7.11 (Nov. 2018): pp. 2497-2506.
Dhami et al., Biomineralization of calcium carbonates and their engineered applications: a review, Frontiers in Microbiology, Oct. 29, 2013, vol. 4, Art. 314, pp. 1-13.
CNIPA; Notice of First Office Action mailed Feb. 25, 2023 in Chinese Application No. 202080090976.6.

* cited by examiner

302

Use in Cement Paste, Mortar, and Concrete as a SCM, Aggregate, Filler, or Nucleating Agent (A)

Nanoindentation Modulus (GPa)

50 45 40 35 30

*E. coli* HB101/Ure-Int
*S. pasteurii*
*E. coli* HB101/pRS426

(B)

1: calcium carbonate; 2: calcium phosphate (C) *E. coli* Aggregate (Cross-Section)

Relative Phosphorus Content

Higher 1.0

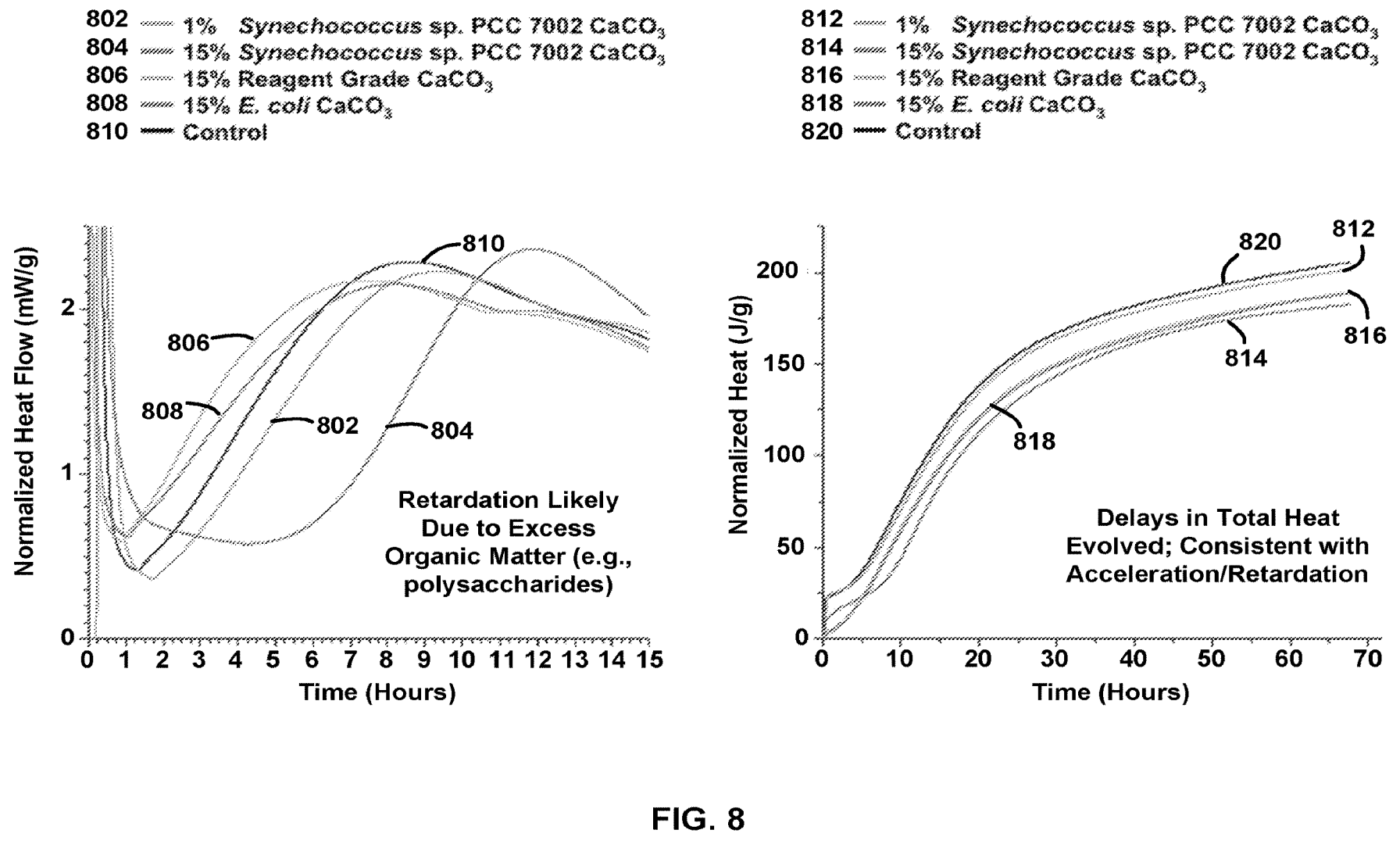

Lower 802 1% *Synechococcus* sp. PCC 7002 $CaCO_3$
804 15% *Synechococcus* sp. PCC 7002 $CaCO_3$
806 15% Reagent Grade $CaCO_3$
808 15% *E. coli* $CaCO_3$
810 Control Normalized Heat Flow (mW/g)

0 1 2

0 1 2 3 4 5 6 7 8 9 10 11 12 13 14 15

Time (Hours)

806 808 802 804 810

Retardation Likely Due to Excess Organic Matter (e.g., polysaccharides)

812 1% *Synechococcus* sp. PCC 7002 $CaCO_3$
814 15% *Synechococcus* sp. PCC 7002 $CaCO_3$
816 15% Reagent Grade $CaCO_3$
818 15% *E. coli* $CaCO_3$
820 Control Normalized Heat (J/g)

0 50 100 150 200

0 10 20 30 40 50 60 70

Time (Hours)

812 820 816 814 818

Delays in Total Heat Evolved; Consistent with Acceleration/Retardation

FIG. 8

METHODS OF FORMING MINERALS USING BIOMINERALIZING MICROORGANISMS AND BIOMINERALIZING MACROORGANISMS AND COMPOSITIONS FORMED USING SAME

CROSS-REFERENCE TO RELATED APPLICATIONS

This application is a U.S. national stage entry under 35 U.S.C. § 371 of International Application No. PCT/US2020/058344 entitled METHODS OF FORMING MINERALS USING BIOMINERALIZING MICROORGANISMS AND BIOMINERALIZING MACROORGANISMS AND COMPOSITIONS FORMED USING SAME filed Oct. 30, 2020 which claims the benefit of U.S. Provisional Application No. 62/928,944, entitled METHODS OF USING BACTERIA FOR PRODUCING MATERIALS SUITABLE FOR USE IN CEMENT PASTE AND CONCRETE AND MATERIALS FORMED USING SAME and filed Oct. 31, 2019, the contents of which are hereby incorporated herein by reference to the extent such contents do not conflict with the present disclosure

STATEMENT REGARDING FEDERALLY-SPONSORED RESEARCH OR DEVELOPMENT

This invention was made with government support under grant number HR0011-17-2-0039, awarded by DOD/DARPA. The government has certain rights in the invention.

FIELD OF THE DISCLOSURE

The disclosure generally relates to methods of using biomineralizing microorganisms and/or biomineralizing macroorganisms in the manufacture of materials, such as cement, concrete, and others. The disclosure also relates to materials and compositions formed using biomineralizing microorganisms and macroorganisms.

BACKGROUND OF THE DISCLOSURE

Concrete, generally a mixture of water, aggregates, and ordinary portland cement (OPC), is one of the most consumed materials on Earth, and the economic and environmental consequences of its ubiquity are significant. The production of OPC alone accounts for an estimated 4 to 8.6% of global $CO_2$ emissions. As the global population continues to rise, cement production is estimated to increase by about 50% by 2050 to keep pace with new and aging infrastructure demands in both developing and developed countries.

Cement is typically produced by heating limestone together with clay to temperatures in excess of 1500° C.—an energy intensive process that produces large calcium silicate mineral aggregates, referred to as clinker. The reaction often takes place in kilns that are heated using carbon-based fuels, such as coal, natural gas, oil, or coke, which produces significant $CO_2$ emissions. The clinker is subsequently ground into fine powders using another energy-intensive process. The dry, ground powders are used to make concrete.

Cement paste, which includes cement and water, typically comprises about 10% of concrete by volume, but accounts for about 95% of concrete $CO_2$ emissions (due to fuel combustion and the chemical calcination of limestone). Aggregates (e.g., limestone, gravel, sand) comprise the remaining volume. Improved techniques for forming cement, concrete, and other materials that produce less $CO_2$ are desired.

Concrete and/or cement can also include additives, such as silicon dioxide, calcium dioxide, calcium carbonate, or the like. The additives can be formed by grinding source materials, which can add to the $CO_2$ emissions associated with cement and concrete production. Accordingly, improved methods of producing such additives are also desired.

Any discussion of problems and solutions involved in the related art has been included in this disclosure solely for the purposes of providing a context for the present invention and should not be taken as an admission that any or all of the discussion was known at the time the invention was made.

SUMMARY OF THE DISCLOSURE

Various embodiments of the present disclosure relate to methods of forming mineral particles for use in a variety of applications and to compositions including the mineral particles. While the ways in which various embodiments of the present disclosure address drawbacks of prior techniques are discussed in more detail below, in general, various embodiments of the disclosure provide improved methods for forming mineral particles and compositions, including the mineral particles, that produce significantly less carbon dioxide and may even consume more carbon dioxide than the methods produce. In other words, exemplary methods or portions thereof may be carbon negative. Further, examples of the disclosure allow one to tailor a morphology and/or properties of mineral particles, which allows for tuning of desired properties in compositions (e.g., cement and/or concrete) including such particles.

In accordance with various examples of the disclosure, a method of forming a composition, such as a cement paste, is disclosed. The method includes providing a growth medium, providing one or more of biomineralizing microorganisms and biomineralizing macroorganisms, producing mineral particles using the one or more of biomineralizing microorganisms and biomineralizing macroorganisms, and forming the cement paste using the mineral particles. The biomineralizing microorganisms can include bacteria, such as, for example, cyanobacteria. Additionally or alternatively, the biomineralizing microorganisms can include microalgae, such as, for example, diatoms and/or coccolithophores. By way of examples, the bacteria can be used to produce calcium carbonate and/or the microalgae can be used to produce calcium carbonate and/or silicon dioxide. As discussed in more detail below, various parameters, such as bacteria specie, microalgae specie, time, temperature, media chemistry, light/dark conditions, and gas environment (i.e., $CO_2$, air), and the like can be used to tune desired properties of the biomineralizing microorganisms. The mineral particles produced in accordance with examples of the disclosure can be used in a variety of applications, including the cement paste, mortar, and concrete—as an aggregate, filler, nucleating agent, supplementary cementitious materials, or the like.

In accordance with further examples of the disclosure, a method of forming a concrete composition is provided. The method can include additional steps, such as grinding the mineral particles to an average particle size of, for example, about 1 to about 100 um to form a powder, heating the ground particles with other additives to a temperature of greater than 1500° C. to form clinker, and grinding the clinker to form portland cement.

In accordance with further examples, a cement paste composition is formed according to a method described herein. The mineral particles can be used or included as a direct additive to a cement paste and/or as a replacement for limestone, sand, or the like during the production of cement.

In accordance with further examples of the disclosure, a concrete composition can include a cement paste as described herein and additional components. For example, the concrete composition can additionally include coarse aggregate, fine aggregate, and one or more other solid compounds, such as fly ash, slag, other natural or synthetic pozzolans, fibers, and/or one or more liquid admixtures.

In accordance with further examples of the disclosure, a method of forming a mineral is provided. The method can include providing a growth medium, providing one or more microorganisms comprising one or more of bacteria and microalgae—e.g., cyanobacteria, diatoms, and/or coccolithophores, and producing mineral particles using the growth medium and the one or more microorganisms. Minerals produced using the method can be used for forming one or more of paints, coatings, and drywall, as a white pigment, as a source for lime material, as lime material, as agricultural lime, and/or as a calcium source.

These and other embodiments will become readily apparent to those skilled in the art from the following detailed description of certain embodiments having reference to the attached figures; the invention not being limited to any particular embodiment(s) disclosed.

BRIEF DESCRIPTION OF THE DRAWING FIGURES

A more complete understanding of exemplary embodiments of the present disclosure can be derived by referring to the detailed description and claims when considered in connection with the following illustrative figures.

FIG. 8 illustrates isothermal calorimetry data, namely (a) heat flow and (b) total evolved heat, of biogenic $CaCO_3$ nano-fillers in OPC paste in accordance with examples of the disclosure.

It will be appreciated that elements in the figures are illustrated for simplicity and clarity and have not necessarily been drawn to scale. For example, the dimensions of some of the elements in the figures may be exaggerated relative to other elements to help improve understanding of illustrated embodiments of the present disclosure.

DETAILED DESCRIPTION OF EXEMPLARY EMBODIMENTS

Although certain embodiments and examples are disclosed below, it will be understood by those in the art that the invention extends beyond the specifically disclosed embodiments and/or uses of the invention and obvious modifications and equivalents thereof. Thus, it is intended that the scope of the invention disclosed should not be limited by the particular disclosed embodiments described below.

Various examples of the present disclosure generally relate to methods of forming mineral particles using one or more of biomineralizing microorganisms and biomineralizing macroorganisms and to compositions and products formed using the mineral particles. Exemplary methods described herein can reduce an amount of carbon dioxide otherwise emitted during the manufacture of the compositions and products. Several examples described below relate to the formation of cement and concrete. However, unless otherwise noted, the invention is not limited to such examples.

Mineral particles, such as calcium carbonate, silicon dioxide, and the like, can be added to compositions, such as cement, cement paste, and/or concrete. The mineral particles can be used as an additive or as a replacement for limestone, sand, or the like, and can be subject to further processing to form cement, such as portland cement.

In accordance with examples of the disclosure, biomineralizing microorganisms and biomineralizing macroorganisms produce siliceous (i.e., silica-containing) and calcareous (i.e., calcium-containing) minerals suitable for use as an additive and/or as a limestone replacement for use in cement, concrete, and other compositions and products.

Figure 1:
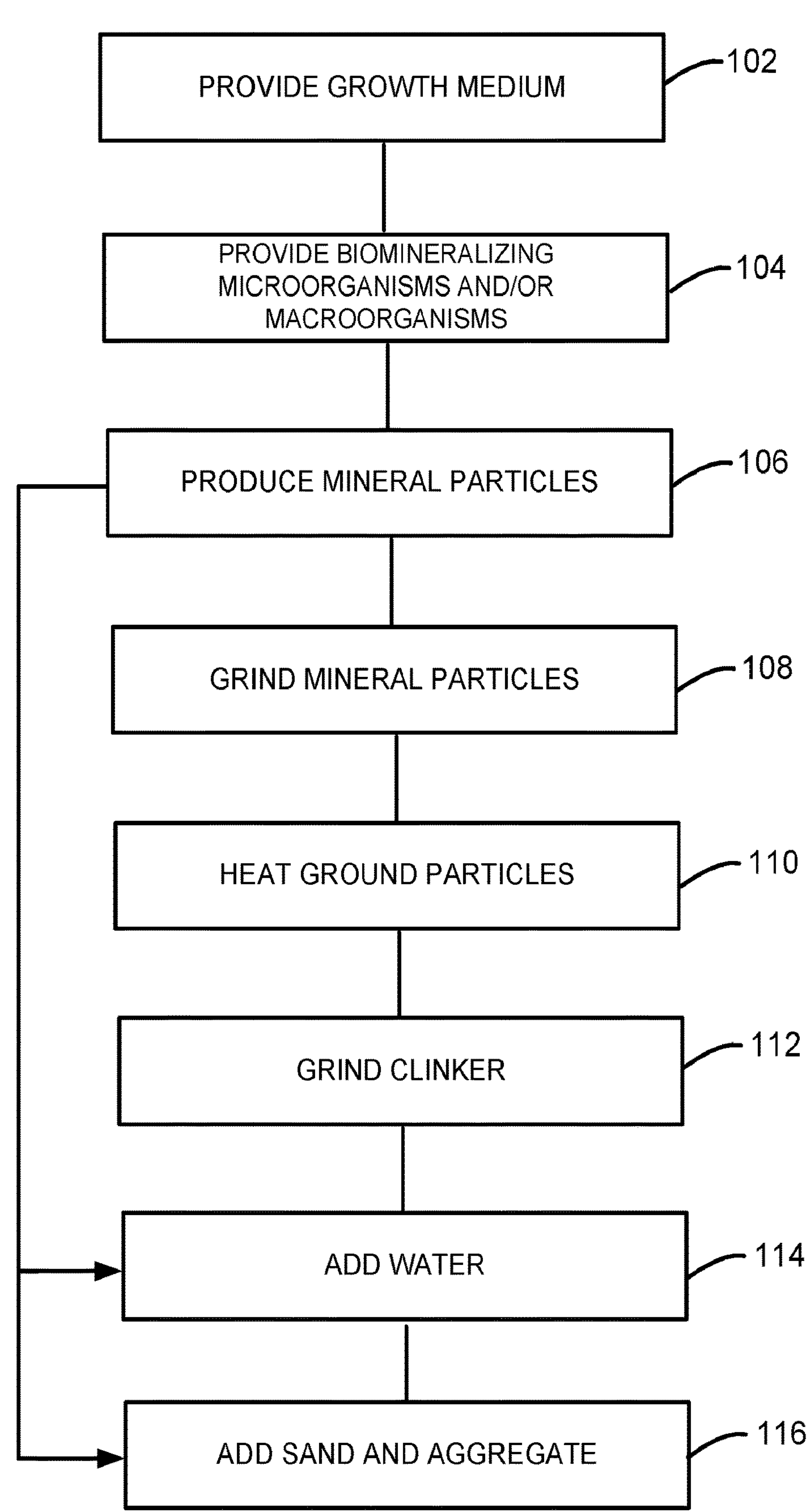
FIG. 1 illustrates a method in accordance with examples of the disclosure.

FIG. 1 illustrates a method 100 in accordance with various examples of the disclosure. Method 100 includes the steps of providing a growth medium 102, providing biomineralizing microorganisms and/or biomineralizing macroorganisms 104, producing mineral particles 106, grinding the mineral particles 108, heating the ground mineral particles 110, grinding clinker 112, adding water 114, and adding sand and aggregate 116. Although illustrated with steps 102-116, methods in accordance with the disclosure can include a subset of these steps (e.g., in the formation of cement and cement paste) and/or include additional or alternative steps.

During step 102, a suitable growth medium for the growth and/or biomineralizing microorganisms and biomineralizing macroorganisms is provided. The growth medium can depend on the biomineralizing microorganisms and biomineralizing macroorganisms provided and/or desired polymorphs and/or properties of the formed mineral particles. For example, in the case of cyanobacteria, the growth medium can include seawater and $CO_2$ from the atmosphere (e.g., in the form of carbonic acid) to produce $CaCO_3$. A $CaCl_2$ medium in which nickel, ampicillin, and Ca2+ are added can be used for recombinant *E. coli* strains (see Liya Liang et al., Rational Control of Calcium Carbonate Precipitation by Engineered *Escherichia Coli*, ACS Synth. Biol. 2018, 7, 2497-2506, the contents of which are hereby incorporated herein by reference to the extent such contents do not conflict with the present disclosure). A similar medium, without the nickel, can be used for *S. pasteurii* biomineralization (see Chelsea M. Heveran et al., Engineered Ureolytic Microorganisms Can Tailor the Morphology and Nanomechanical properties of Microbial-Precipitated Calcium Carbonate, Scientific Reports 1(2019) 9:14721), the contents of which are hereby incorporated herein by reference to the extent such contents do not conflict with the present disclosure). BG-11 can be used as a growth medium for microalgae, such as diatoms and coccolithophores.

During step 104, one or more of biomineralizing microorganisms and biomineralizing macroorganisms are added to the growth medium provided during step 102. The one or more of biomineralizing microorganisms and biomineralizing macroorganisms can include bacteria, such as cyanobacteria and/or microalgae, such as diatoms and/or coccolithophores.

During step 106, mineral particles are produced using the one or more of biomineralizing microorganisms and biomineralizing macroorganisms provided during step 104. The mineral particles can be or include, for example, one or more of calcium carbonate or silicon dioxide. More particularly, the mineral particles can include amorphous silicon dioxide or crystalline calcium carbonate. By way of particular examples, the biomineralizing microorganisms comprising coccolithophores or bacteria can be used to form mineral particles comprising calcium carbonate and/or the biomineralizing microorganisms including diatoms can be used to form mineral particles including silicon dioxide and/or calcium carbonate. A size of the formed mineral particles can range from about 10 nm to about 5 mm or about 10 nm and about 1 um or about 1 um and about 5 mm.

As discussed in more detail below in connection with the examples, a morphology and/or other properties of mineral particles can be controlled and/or manipulated by manipulating one or more of the biomineralizing microorganisms and biomineralizing macroorganisms, the growth medium (e.g., $CaCl_2$ in the growth medium), temperature, time, and the like. For example, in some cases, a morphology of the mineral particles is rounded. In other cases, a morphology of the mineral particles is angular. Further, a size of the mineral particles can be controlled and/or manipulated by manipulating one or more of the same or similar parameters—e.g., to the size ranges noted above. In some cases, the mineral particles can be pressed together to form larger particles having an average cross-sectional dimension of up to about 5 cm.

The mineral particles produced during step 106 can be used as an additive to compositions, such as cement, cement paste, or concrete. When used as an additive in the formation of concrete, the mineral particles can be added during, for example, step 114 and/or step 116. Additionally or alternatively, the mineral particles can be used as a cement precursor (e.g., as ground limestone replacement or as silicon source). In these cases, method 100 can proceed to step 108.

During step 108, mineral particles formed during step 106 and/or other material, such as calcium sources (e.g., limestone, chalk, marl, seashells, aragonite, and the like) and silicon, aluminum, and iron, and the like, which can be obtained from ores and minerals, such as sand, shale, clay, and iron ore, can be ground. For example, the mineral particles can be ground to an average particle size of about 1 to about 100 μm to form a powder.

During step 110, the ground particles are heated to form clinker, which are gray, glass-hard, spherically-shaped nodules that typically range from 0.32 to 5.1 centimeters (cm) in diameter.

During step 112, the clicker is ground and can be blended with other materials to form portland cement. Up to about 5 percent gypsum and/or natural anhydrite is added to the clinker during step 112 to control the cement setting time, and other desired properties.

Water can be added to the portland cement formed during step 112 to form cement paste during step 114. An amount of cement in the cement paste can range from about 20 to about 90 or about 30 to about 80 weight percent. Unless noted otherwise, all percentages set forth herein are in weight percent.

The cement paste can be combined with or mixed with fine aggregate and coarse aggregate during step 116 to form concrete.

The coarse aggregate can include, for example, crushed stone, river gravel, or the like. A cross-sectional dimension of the coarse aggregate can be greater than 4.5 mm or range from about 4 to about 130 or about 5 to about 50 mm. The concrete composition can include about 15 to about 60, about 25 to about 50, or about 30 to about 45 wt % of the coarse aggregate.

The fine aggregate can include, for example, sand, manufactured fine aggregate (e.g., using mineral particles formed in accordance with the disclosure), or the like. A cross-sectional dimension of the fine aggregate can be less than 4.5 mm or range from about 0.002 to about 4.5 or about 0.2 to about 4.5 mm. The concrete composition can include about 15 to about 50, about 25 to about 45, or about 25 to about 40 wt % of the fine aggregate.

The concrete can include a cement as described above. In accordance with examples of the disclosure, the concrete composition can include about 1 to about 30, about 3 to about 20, or about 5 to about 10 wt % of the cement.

Specific Examples

The examples provided below illustrate methods of forming calcium carbonate and silicon oxide suitable for use in, for example, the formation of cement and concrete. These examples are meant to illustrate embodiments of the disclosure, and are not meant to limit the scope of the disclosure or claims.

Calcium Carbonate Examples from Native and Engineered Bacteria

Limestone, a common aggregate in concrete, is composed primarily of $CaCO_3$, of which 44% (by mass) is, in effect, sequestered $CO_2$. Geological limestone deposits (and quarries thereof) formed over millennia predominantly by the biological mechanism microbial-induced $CaCO_3$ precipitation (MICCP). Based on this, it is thought that more $CO_2$ could be stored in concrete than is emitted during its production by exploiting and accelerating the biological mechanism of MICCP using synthetic biology to produce aggregates suitable for use in cement paste, mortar, and concrete. Additionally or alternatively, biomineralizing microorganisms and biomineralizing macroorganisms can be used in the production of nano- and/or micro-fillers.

Crushed limestone ($CaCO_3$) is widely used as a mineral admixture and cement replacement. Up to 15% by weight of limestone is used in portland-limestone cement (PLC) in the US and up to 35% in Europe. When it is sufficiently fine (<10 μm), $CaCO_3$ imparts desirable characteristics to fresh- and hardened-state properties of cement paste. However, larger (>10 μm) particles can negatively impact properties. These effects can be attributed to the size, morphology (e.g., shape, polymorph), and gradation of $CaCO_3$. To be functional and suitable for use in OPC concrete, $CaCO_3$ nano-fillers should be of sufficient size and micro-fillers should be of sufficient shape. Exerting metabolic control during biological $CaCO_3$ precipitation can be used to produce carbon-storing nano- and micro-fillers from, for example, waste $CO_2$ that are suitable for use in OPC concrete.

In fresh OPC concrete, limestone nanoparticles can affect rheology, hydration, chemical shrinkage, and mineral formation. Nano-fillers can improve cement flow by reducing inter-particle friction and enabling entrapped water to flow better, while larger micro-fillers increase water demand by negatively impacting workability. Workability problems can be exacerbated when crushed, angular limestone is used as a micro-filler. Using $CaCO_3$ as fine aggregate, for example, can increase water demand, and the larger angular particles decrease cohesion and increase bleeding. Additionally, limestone nanoparticles can provide nucleation sites for calcium silica hydrate (CSH), thereby accelerating hydration and time to set, while larger particles are relatively inert. This phenomenon is attributed to both the particle size and the increased packing density achieved by nanoparticles. Cement pastes that contain larger limestone particles typically exhibit lower degrees of hydration. Cements containing limestone nano-fillers are, however, susceptible to chemical shrinkage due to the speed of hydration, while cements with crushed limestone aggregate are reported to have higher plastic shrinkage due to the evaporation of bleed water. Lastly, $CaCO_3$ nano-fillers can react with cements that have a high C3A content to form crystalline monocarboaluminate hydrate that, in Type II cements, can lead to increased compressive strength. In hardened OPC concrete, properties like porosity and compressive strength also depend on the particle shape and size of the limestone mineral addition. Porosity is reduced when limestone nanoparticles are added into the mixture, thereby diminishing water absorption and other properties, like chloride diffusion. However, larger limestone particles increase pore volume and void space, leading to increased water absorption and gas permeability and reduced resistance to chloride ion penetration. Furthermore, nanoparticles increase the initial compressive strength of OPC concrete, again, due to increased nucleation of reaction products. While using limestone as a sand replacement improves OPC concrete compressive and flexural strength in small percentage replacements (due to improvements to the interfacial transition zone (ITZ) and interlocking of aggregate particles), extensive replacement of sand by rough, angular limestone micro-fillers decreases compressive strength, regardless of cement type (e.g., Type I/II, Type III).

Bacterial Production of $CaCO_3$

Desired shapes and sizes of calcium carbonate can be obtained by selecting (1) bacteria species, (2) media chemistry, and/or (3) genetically modified bacteria strains that can use $CO_2$ and a source of elemental calcium in the media to produce $CaCO_3$ precipitates.

Figure 5:
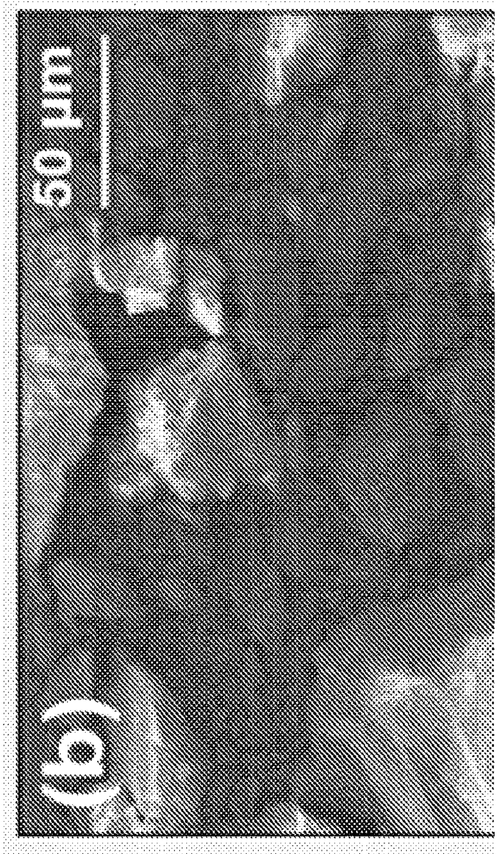
FIG. 5 illustrates SEM images of common ground limestone used as (a) nano-filler cement replacement and (b) micro-filler fine aggregate replacement, as well as (c) angular and (d) round $CaCO_3$ particles grown in seawater and high $CO_2$ that have been produced using biomineralizing microorganisms, namely, cyanobacteria (*Synechococcus*) in accordance with examples of the disclosure.
Figure 5:
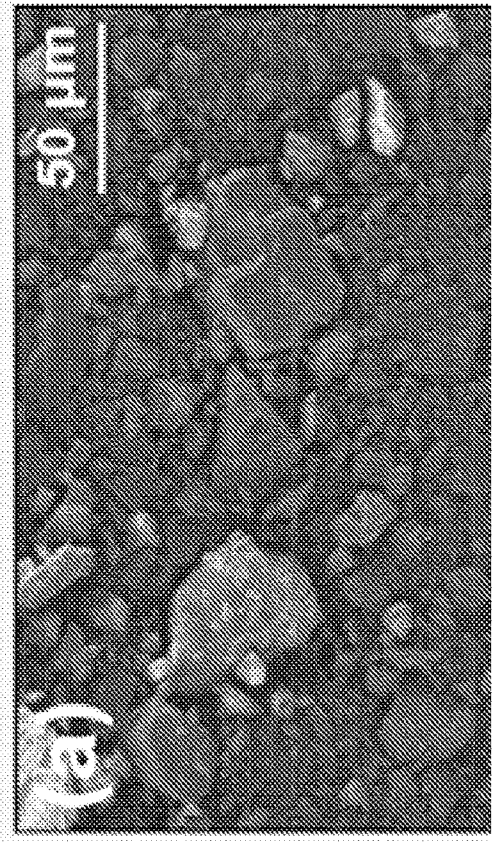
Figure 5:
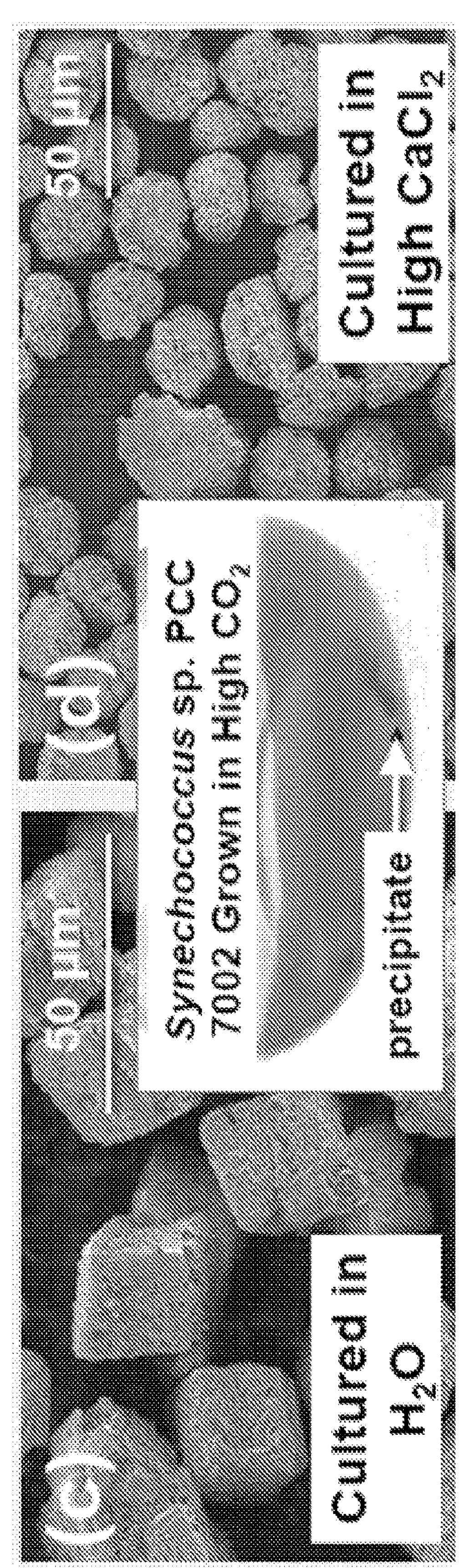

Examples of media-controlled tailorability of $CaCO_3$ is shown in FIG. 5, which illustrates that cyanobacteria (e.g., *Synechococcus* sp. PCC 7002, a photosynthetic carbon-sequestering that uses calcium present in seawater (its growth media) and $CO_2$ from the atmosphere), can architect $CaCO_3$ precipitates with different shapes and sizes. With additional calcium in the media (e.g., at concentrations of greater than 1 g/L $CaCl_2$ or between about 30 g/L $CaCl_2$ and about 120 g/L $CaCl_2$), *Synechococcus* will precipitate more rounded crystals—an important result that can be used to fine-tune carbon-storing $CaCO_3$ particles suitable for cement paste.

Figure 6:
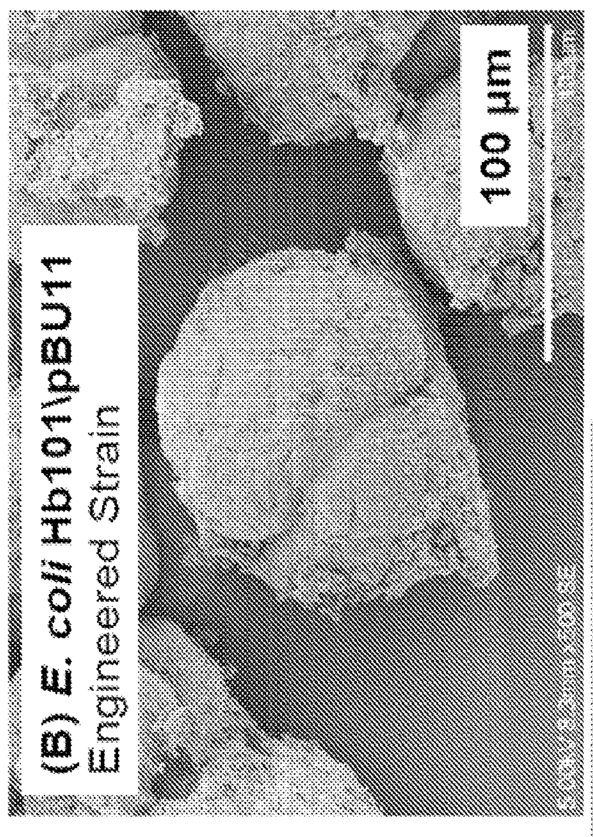
FIG. 6 illustrates $CaCO_3$ mineral particles formed from ureolytic *S. pasteurii* and genetically engineered urease expression strains of *E. coli* in accordance with examples of the disclosure.
Figure 6:
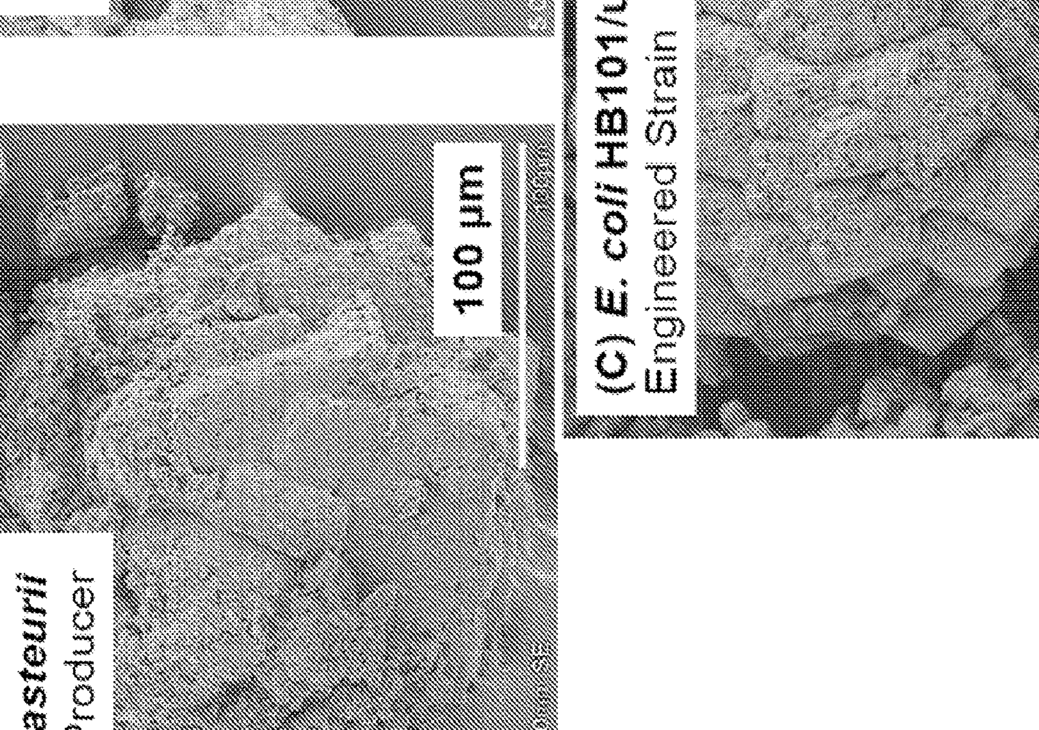

Different bacteria use different metabolic pathways to produce biogenic $CaCO_3$. For example, instead of photosynthesis, *S. pasteurii* produces urease, an enzyme that hydrolyzes urea. Through subsequent reactions (and, again, in the presence of calcium), $CaCO_3$ is formed. We have shown that the urease pathway can be introduced into non-native producers (e.g., *E. coli*) that are more genetically tractable (i.e., modifiable). By modifying the number of plasmids that were introduced into the genome, not only did we show that a non-native producer can precipitate $CaCO_3$, we also showed that we can tailor the morphology of biogenic $CaCO_3$. FIG. 6 shows SEM images of $CaCO_3$ precipitates obtained in accordance with examples of the disclosure that demonstrate the feasibility of tailoring $CaCO_3$ morphology and particle size using different microbial species and genetically modified strains within the same specie (i.e., *E. coli*).

Based on the data in FIGS. 5 and 6, it is thought that *Synechococcus* sp. PCC 7002 produces adequate nano-fillers, given that the concentration of calcium in the A+ media is lower than the other strains and unavailable for further crystal growth in batch reaction conditions. *E. coli* can be used to produce micro-fillers, due to the effectiveness of the urea hydrolysis MICCP mechanism in LB media (which is supplemented with higher concentrations of calcium). It is also thought that lower temperature, and low-salt (i.e., low-ionic-strength—e.g., a concentration of about 1 to about 30 or about 5 to about 25 g/L $CaCl_2$) media will yield larger particles, given that these conditions will slow the kinetics of crystal growth, which will lead to larger, tougher, and stronger precipitates. Examples of adjustable parameters that can be manipulated to obtain desired $CaCO_3$ precipitate properties are provided in Table 1.

TABLE 1

| Species | Example Growth Media | Time | Temperature ° C. |
|---|---|---|---|
| *Synechococcus* | A+ | 0-7 days | 20-40 |
| *Prymnesium* | BG-11 | 0-7 days | 20-40 |
| *Emiliania* | BG-11 | 0-7 days | 20-40 |
| *Sporosarcina* | BPU | 0-7 days | 20-40 |
| *E. coli*-Ure-Int-1 | LB Broth | 0-7 days | 20-40 |
| *E. coli*-Ure-Int-2 | LB Broth | 0-7 days | 20-40 |
| *E. coli*-Ure-Int-3 | LB Broth | 0-7 days | 20-40 |

Cultures of all bacteria are grown in their respective media (see examples in Table 1). For *Synechococcus* sp. PCC 7002, which undergoes MICCP via autotrophic photosynthesis, cells grown to exponential phase can be used for inoculating A+ growth media. These cultures can be incubated at 37° C. in high $CO_2$ (3%) with 100 μmol m-2 s-1 light intensity for 48 h. For organisms that undergo MICCP via urea hydrolysis (e.g., *S. pasteurii, E. coli*), cells can be inoculated into 25 mM of urea-$CaCl_2$ media to a final concentration of 1×107 cells/mL, in which nickel (5 μM) and ampicillin (100 μg/mL) can be supplemented for the *E. coli* strains. All examples can be carried out aerobically in a shaker. Urease Activity (Sigma-Aldrich, MAK120) and Ca2+ Colorimetric Assays (Sigma-Aldrich, MAK022) can be used to monitor urease activity and Ca2+ concentration.

It is thought that *Synechococcus* sp. PCC 7002 (autotrophic photosynthesis) will produce Type A $CaCO_3$ particles, while *S. pasteurii* and *E. coli* (urea hydrolysis) will produce Type A, B, and C $CaCO_3$ particles, as classified according to ASTM C1797 classification of ground $CaCO_3$ particles for use in hydraulic cement.

Figure 7:
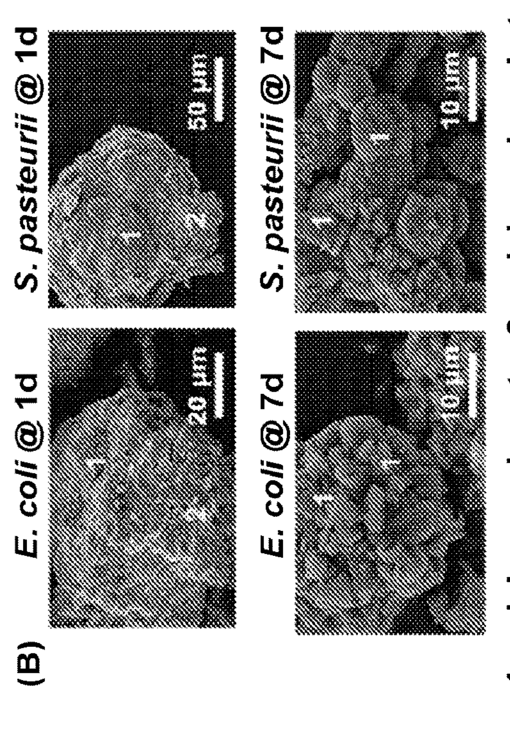
FIG. 7 illustrates (a) nanomechanics of biogenic $CaCO_3$ particles; (b) EDS data of early- and late-age particles produced by *E. coli* and *S. pasteurii*; (c) electron microprobe analysis (EMPA) of a biogenic $CaCO_3$ particle showing phosphorus-rich core in accordance with examples of the disclosure.
Figure 7:
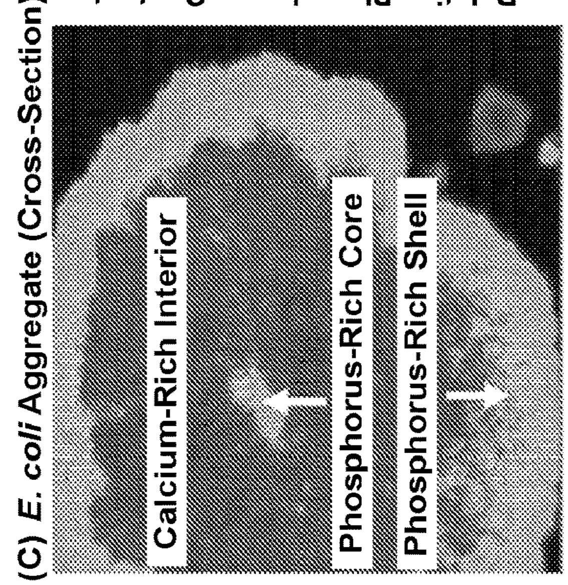

$CaCO_3$ produced in accordance with examples of the disclosure have shown that biogenic $CaCO_3$ particles may change mechanical properties over time due to the thermodynamic maturation of vaterite to calcite. Therefore, time-dependent changes in mechanical properties of biogenic $CaCO_3$ can be monitored to ensure complete maturation and to inform proper curing and storage conditions. This allows a determination of which bacteria strains (and under which conditions) produce stiff, stable biogenic $CaCO_3$. The data in FIG. 7 illustrate that the bacterial cultures that exhibit slower kinetics of crystal growth yield biogenic $CaCO_3$ that is stiffer than biogenic $CaCO_3$ than those produced by bacteria that exhibit higher precipitation kinetics. Ca2+ colorimetric assays can be used to monitor Ca utilization, which is conventionally used as a proxy for the kinetics of biomineralization. Slower kinetics of crystal growth thermodynamically lead to larger and more mechanically robust precipitates. In particular, FIG. 7 illustrates (a) Nanomechanics of biogenic $CaCO_3$ particles; (b) EDS data of early- and late-age particles produced by *E. coli* and *S. pasteurii*; (c) Electron microprobe analysis (EMPA) of a biogenic $CaCO_3$ particle showing phosphorus-rich core. Data show that calcium phosphate can play an important role in biogenic $CaCO_3$ nucleation and termination in these species, while calcium plays a role in $CaCO_3$ growth. These data support the conclusion that slower precipitation kinetics (as measured for *E. coli* HB101/pRS462) may enable production of larger, mechanically stiffer particles.

Physical and chemical properties to cement-relevant surface-charge properties of biogenic $CaCO_3$ particles, such as Point Zero Charge (PZC) can be determined by the pH drift method. 50 ml polypropylene tubes, containing 25 ml of 0.1 M NaCl, can be pH-adjusted to between pH 2-10 with either NaOH or HCl under $N_2$ atmosphere. 50 mg of biogenic $CaCO_3$ can be added to each of these solutions and mixed for 48 h, after which, the pH can be recorded. The PZC, which can be determined from the solution that experienced no change from its initial pH, can be used to explain the rheological properties of cement paste and mortar with biogenic $CaCO_3$ particles. The results can be compared with PZC of commercially ground limestone. Given that a locally high pH (>8) is generally desired for bacterial precipitation of $CaCO_3$ for both autotrophic photosynthetic and urea hydrolytic MICCP mechanisms, it is thought that PZC will be higher for biogenic $CaCO_3$ than conventional limestone, which is beneficial for the rheological properties of cement paste and mortar, given that the pH of cement paste >12.

The biogenic $CaCO_3$ formed in accordance with examples of the disclosure can affect the workability, chemical shrinkage, rheological, heat of hydration, set-time, and other properties of fresh cement pastes. By way of examples, 1%, 5%, 10%, 15%, or any range between such values, of $CaCO_3$ formed in accordance with examples of the disclosure, can be used to replace cement in cement pastes.

Workability can be measured using a mini-slump cone. Chemical shrinkage can be measured by monitoring changes in geometry after final set. Time-dependent rheological properties (i.e., storage modulus, loss modulus) can be measured by small-amplitude oscillatory shear (SAOS) testing using an Anton Paar MCR 301 Rheometer. Zeta-potential (ZP) can be interrogated via phase analysis light scattering using a ZETA PLUS ZP analyzer. Setting time can be studied using standardized setting-time tests using a Vicat needle, in which initial and final set will be determined. Measurements of setting time can be correlated with heat of hydration measurements, which can be analyzed using a TAM Air Isothermal calorimetry (IC) system. Results can be correlated with physical and chemical properties of nano-filler particles that are obtained in accordance with examples of the disclosure. It is thought that biogenic $CaCO_3$ nano-fillers formed in accordance with examples described herein act as nucleating agents for cement paste (higher CH, CSH content) and improve rheology without compromising setting in small doses (5-15% by mass of cement). Combinations of smooth and angular particles are likely to inhibit chemical shrinkage caused by angular nano-fillers alone. Finally, residual organic matter may retard hydration, as evidenced by set-time delays shown in FIG. 8.

Biogenic $CaCO_3$ formed in accordance with examples of the disclosure can also be used to replace sand in mortars. Biogenic $CaCO_3$ micro-fillers (e.g., >10 μm) can affect the workability, rheological, heat of hydration and set-time properties of fresh OPC mortars. Systematic replacement of sand can be from, for example, 0% or greater than 0% to 10%. Workability can be measured using a mini-slump cone test. Rheological properties (i.e., yield stress, viscosity) and ZP will be measured using an Anton Paar MCR 301 rheometer outfitted with a building materials cell and a ZETA PLUS ZP analyzer, respectively. Setting time can be studied (as it was for cement pastes) using standardized setting-time tests using a Vicat needle. Measurements of setting time can be correlated with heat of hydration measurements, which will be analyzed using a TAM Air IC system. It is thought that the mini-slump of mortars will increase, while shear strength, viscosity, and ZP will improve with the use of round vs. angular biogenic $CaCO_3$ particles. It is also thought that angular sand-sized particles accelerate set-time and cement hydration kinetics.

FIG. 8 illustrates Isothermal calorimetry data, namely (a) heat flow (represented by lines 802-810) and (b) total evolved heat of biogenic $CaCO_3$ nano-fillers (represented by lines 812-820) in OPC paste. While biogenic $CaCO_3$ nano-fillers from *E. coli* act similar to OPC (and, in some instances, accelerate hydration), biogenic $CaCO_3$ nano-fillers from *Synechococcus* sp. PCC 7002 retard hydration—a result that is likely due to excess organic matter, like polysaccharides (i.e., sugars), which can be mitigated by pre-conditioning particles prior to use in cement paste.

Hardened-state properties (i.e., mineralogy, microstructure, porosity, mechanical properties) of (1) cement pastes with biogenic $CaCO_3$ nano-fillers, (2) cement mortars with biogenic $CaCO_3$ nanofillers and biogenic micro-scale particles and (3) cement-based concrete with $CaCO_3$ inert cement fillers and fine-aggregate replacement can be manipulated in accordance with examples of the disclosure. Reaction products (e.g., CH, CSH, ettringite) can be analyzed via semi-quantitative XRD (with an internal standard), which will quantitatively determine relative changes, if any, to the resulting mineralogy of the cementitious binders. Results can be corroborated with a combination TGA-FTIR system to aid identification of amorphous hydrated phases. Changes in microstructure and porosity can be quantified via SEM, XRM, and BET analysis. Finally, mechanical properties, such as elastic modulus and compressive strength, of cement mortars can be measured via mechanical testing according to ASTM C109. It is thought that the angular nano-fillers will enhance carbon-aluminate formation and improve porosity and overall compressive strength and that round $CaCO_3$ particles in mortars will overcome the challenges due to angularity of ground $CaCO_3$ (i.e., improve porosity and compressive strength) provided that the biogenic $CaCO_3$ micro-fillers have equal (or improved) porosity to ground $CaCO_3$.

Biomineralization from Microalgae

In addition to or as an alternative to bacteria, microalgae, such as eukaryotic microalgae—e.g., diatoms and coccolithophores, can be used to form siliceous and calcareous mineral particles suitable for cement, concrete, and mortar, as well as other applications, such as those noted herein. Certain eukaryotic microalgae (e.g., diatoms, coccolithophores) possess an ability to photosynthesize and subsequently produce siliceous and calcareous minerals. Biomineralization of these minerals is facilitated by the silica deposition vesicle in diatoms and the coccolith vesicle in coccolithophore. These specialized organelles are highly adept at stimulating the formation of amorphous silica and crystalline calcium carbonate, respectively. What is exceptionally exciting is that both amorphous silica and crystalline calcium carbonate are the mineral building blocks for both tobermorite and jennite minerals that are analogous to the calcium silicate minerals present in ordinary cement. Bioinformatic and analytical techniques, including synthetic biology toolkits, have been established for the discovery of bioproducts in diverse microorganisms, and these methods can also be used to derive information about bioproducts produced by microalgae. Exemplary diatoms include *Cyclotella* sp. diatom with silica frustule, coccolithophore *Prymnesium neolepis* with silica scales, and calcifying coccolithophore *Emiliania huxleyi* with calcium carbonate coccoliths.

Figure 2:
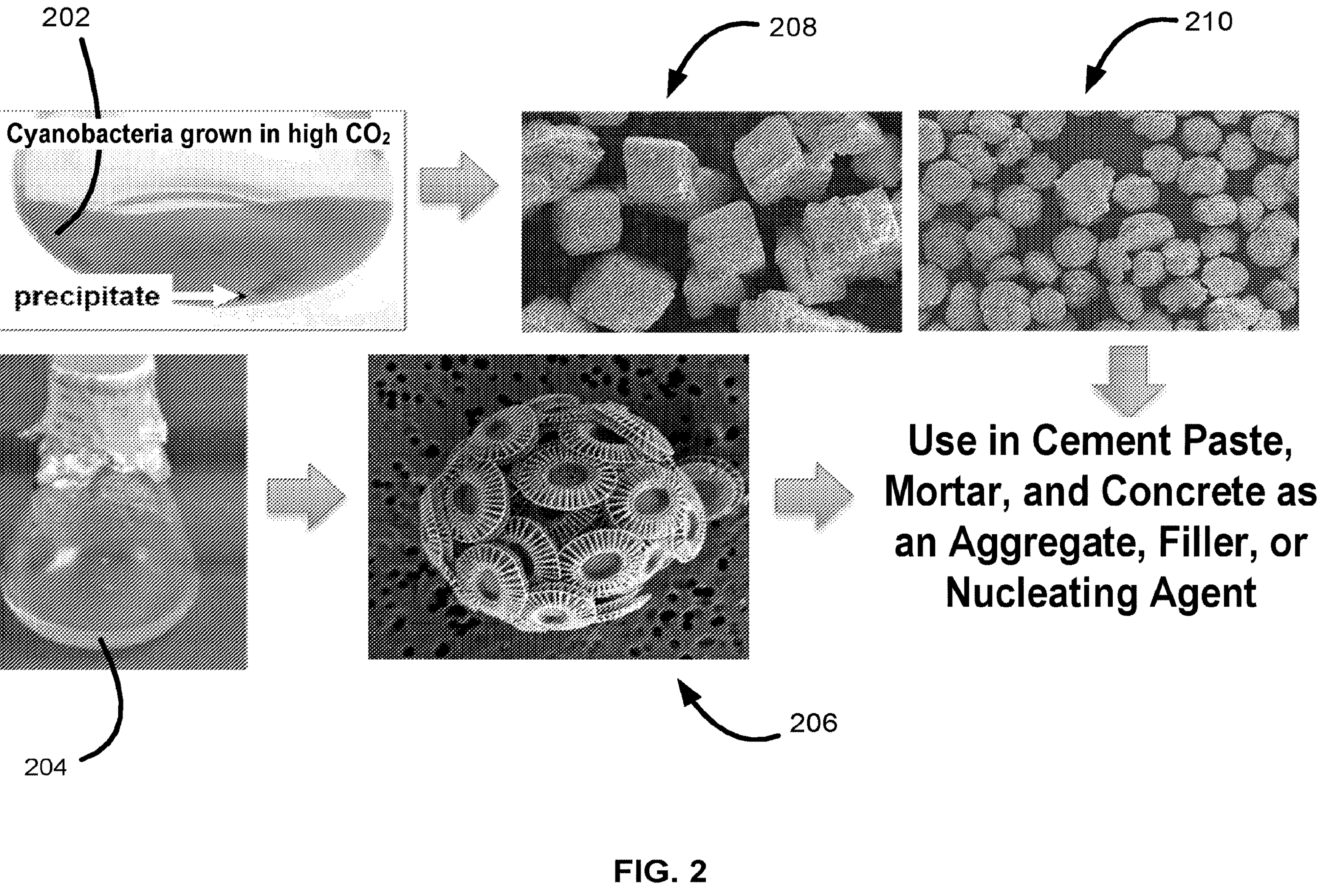
FIG. 2 illustrates mineral particles in accordance with examples of the disclosure.
Figure 3:
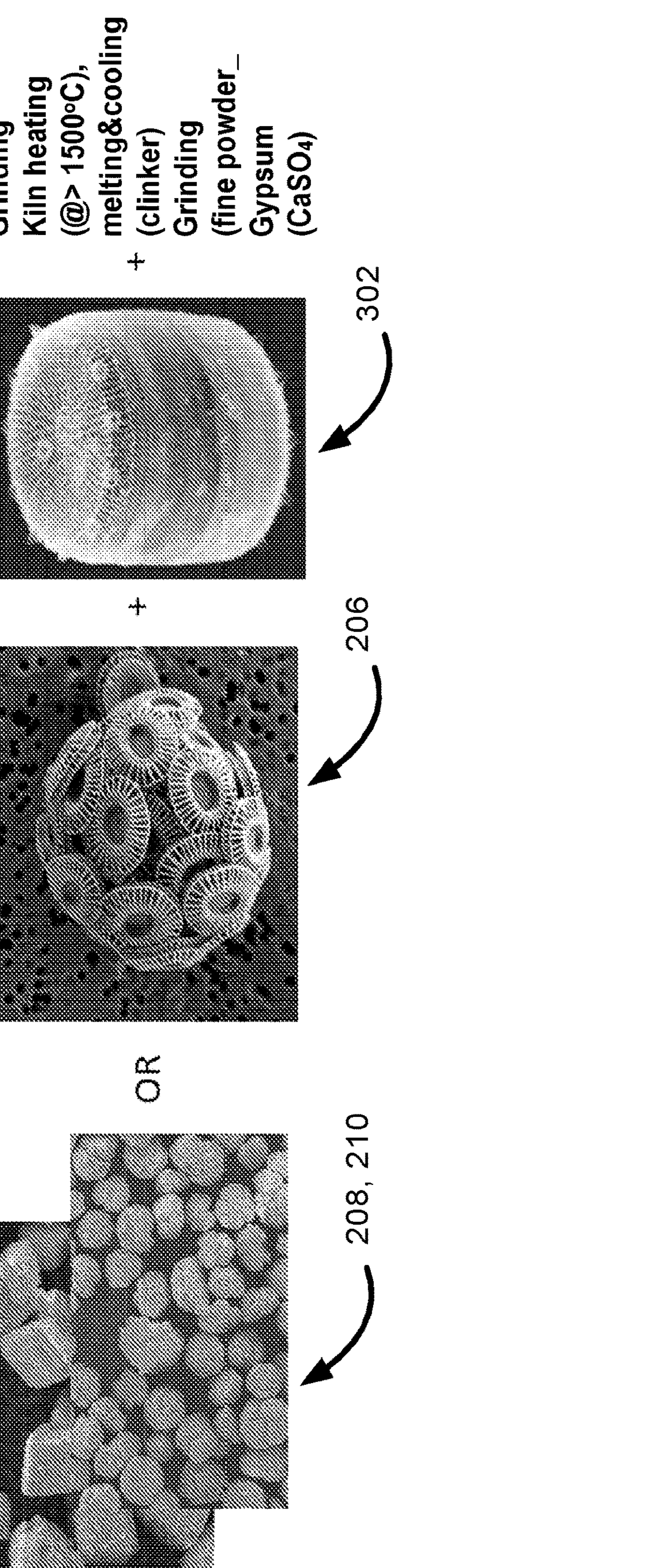
FIG. 3 illustrates mineral particles suitable for use as siliceous and calcareous material in accordance with examples of the disclosure.
Figure 4:
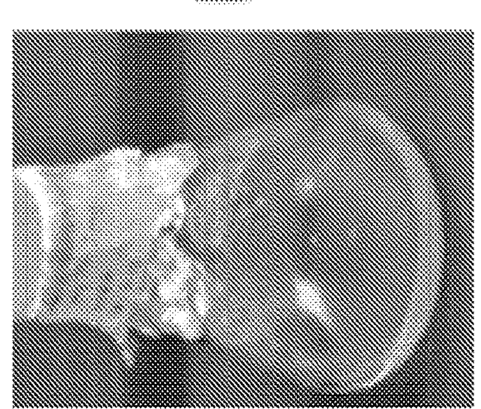
FIG. 4 illustrates mineral particles suitable for use as siliceous material in accordance with examples of the disclosure.
Figure 4:
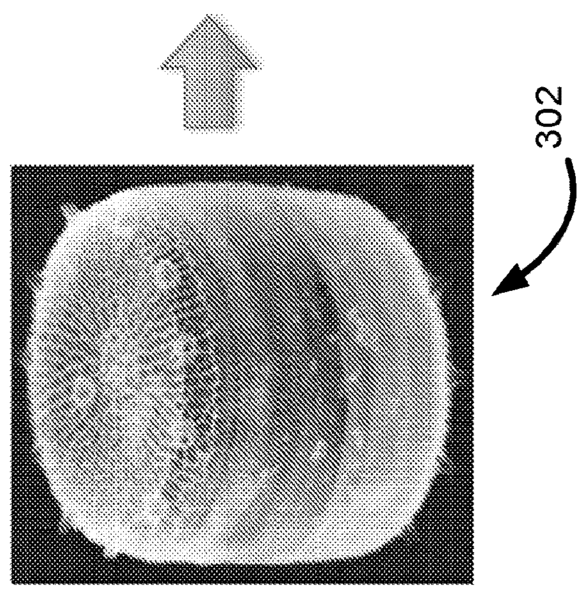
Figure 4:

FIG. 2 illustrates the use of bacteria 202 and microalgae 204 for the production of calcareous mineral particles 206, 208, 210 produced from microalgae 204 and bacteria 202. FIG. 3 illustrates use of calcareous mineral particles 206, 208, 210 and siliceous particles 302. As illustrated in FIG. 3, the mineral particles formed in accordance with examples of the disclosure can be subject to additional processing (e.g., steps 108-116 of method 100) to form cement and/or concrete, as discussed above in connection with FIG. 1. FIG. 4 illustrates use of siliceous material in the production of cement paste, mortar, concrete, and the like.

The present invention has been described above with reference to a number of exemplary embodiments and examples. It should be appreciated that the particular embodiments shown and described herein are illustrative of the preferred embodiments of the invention and its best mode, and are not intended to limit the scope of the invention. Further examples of the disclosure are set forth in the claims. It will be recognized that changes and modifications may be made to the embodiments described herein without departing from the scope of the present invention. These and other changes or modifications are intended to be included within the scope of the present invention.

The invention claimed is:

1. A method of forming concrete, the method comprising the steps of:

providing a growth medium;

providing one or more of biomineralizing microorganisms and biomineralizing macroorganisms within the growth medium;

producing mineral particles using the one or more of biomineralizing microorganisms and biomineralizing macroorganisms within the growth medium by photosynthesis;

separating the mineral particles from the growth medium;

forming portland cement paste using the mineral particles separated from the growth medium; and mixing the cement paste with sand and aggregate, wherein the concrete comprises about 30 to about 45 wt % aggregate, about 25 to about 40 wt % sand, and about 5 to about 10 wt % cement paste, and wherein the mineral particles comprise at least one of amorphous silicon dioxide particles or crystalline calcium carbonate particles.

2. The method of claim 1, wherein the biomineralizing microorganisms within the growth medium comprise bacteria selected from the group consisting of cyanobacteria.

3. The method of claim 1, wherein the biomineralizing microorganisms within the growth medium comprise microalgae.

4. The method of claim 3, wherein the microalgae is selected from the group consisting of diatoms and coccolithophores.

5. The method of claim 1, wherein the growth medium comprises seawater and carbon dioxide.

6. The method of claim 1, wherein a morphology of a first portion of the crystalline calcium carbonate particles is rounded and wherein a morphology of a second portion of the crystalline calcium carbonate particles is angular.

7. The method of claim 1, wherein an average cross-sectional dimension of one or more of the amorphous silicon dioxide particles and the crystalline calcium carbonate particles is between about 10 nm and about 1 um.

8. The method of claim 1, wherein an average cross-sectional dimension of the crystalline calcium carbonate particles is between about 1 μm and about 5 mm.

9. The method of claim 1, wherein the mineral particles are an additive to portland cement paste.

10. The method of claim 1, wherein the crystalline calcium carbonate particles are pressed together to form larger particles having an average cross-sectional dimension of up to about 5 cm.

11. The method of claim 1, wherein the growth medium comprises at least one of A+, BG-11, BPU, or LB Broth and wherein the growth medium comprises about 1 to about 30 g/L $CaCl_2$.

12. The method of claim 1, wherein the crystalline calcium carbonate particles are formed using *Synechococcus* sp. PCC 7002.

13. The method of claim 1, wherein the biomineralizing microorganisms within the growth medium comprise *Emiliania huxleyi.*

14. The method of claim 1, wherein the biomineralizing microorganisms within the growth medium comprise one or more of *Prymnesium neolepis* and *Cyclotella* sp.

15. The method of claim 1, further comprising the steps of:

grinding the mineral particles to an average particle size of about 1 to about 100 μm to form a powder.

16. The method of claim 1, further comprising the steps of:

grinding the mineral particles;

heating the ground particles with other additives to a temperature of greater than 1500° C. to form clinker; and grinding the clinker to form portland cement.

17. The method of claim 16, further comprising a step of:

adding water to the portland cement to form the cement paste.

18. A method of forming cement paste, the method comprising the steps of:

providing a growth medium;

providing one or more of biomineralizing microorganisms and biomineralizing macroorganisms within the growth medium;

producing mineral particles using the one or more of biomineralizing microorganisms and biomineralizing macroorganisms within the growth medium by photosynthesis;

separating the mineral particles from the growth medium;

forming one or more of portland cement and portland cement paste using the mineral particles separated from the growth medium; and mitigating excess organic matter prior to forming one or more of portland cement and portland cement paste using the mineral particles.

* * * * *